United States Patent [19]

Miyoshi et al.

[11] Patent Number: 5,091,013
[45] Date of Patent: Feb. 25, 1992

[54] MOISTURE HOLDING PIGMENT AND A COSMETIC CONTAINING SUCH A PIGMENT

[75] Inventors: Ryota Miyoshi; Isao Imai; Tadashi Sugaya, all of Saitama, Japan

[73] Assignee: Miyoshi Kasei Co., Ltd., Urawa, Japan

[21] Appl. No.: 388,757

[22] Filed: Aug. 3, 1989

Related U.S. Application Data

[63] Continuation of Ser. No. 155,438, Feb. 12, 1988, abandoned.

[30] Foreign Application Priority Data

Feb. 12, 1987 [JP] Japan ................. 62-30496

[51] Int. Cl.⁵ .................... C08K 5/09; A61K 7/00
[52] U.S. Cl. .................. 106/505; 106/499; 106/501; 424/69
[58] Field of Search ........ 106/499, 501, 505; 424/69

[56] References Cited

U.S. PATENT DOCUMENTS

| | | | |
|---|---|---|---|
| 3,545,995 | 12/1970 | Hattori et al. | 106/505 |
| 4,205,997 | 6/1980 | Hesse et al. | 106/308 Q |
| 4,246,040 | 1/1981 | Okumura et al. | 106/505 |
| 4,606,914 | 8/1986 | Miyoshi | 514/943 |
| 4,622,074 | 11/1986 | Miyoshi et al. | 106/308 F |
| 4,640,943 | 2/1987 | Meguro et al. | 106/308 N |
| 4,648,908 | 3/1987 | Takasuka et al. | 106/308 F |
| 4,710,375 | 12/1987 | Takasuka et al. | 106/308 F |
| 4,775,229 | 7/1988 | Armanini | 106/501 |
| 4,775,420 | 10/1988 | Gonnet et al. | 106/501 |

FOREIGN PATENT DOCUMENTS

| | | | |
|---|---|---|---|
| 207026 | 12/1986 | European Pat. Off. | 106/505 |
| 26131 | 2/1984 | Japan | 106/505 |
| 976084 | 11/1964 | United Kingdom | 106/505 |

Primary Examiner—Mark L. Bell
Assistant Examiner—Helene Klemanski
Attorney, Agent, or Firm—Armstrong, Nikaido, Marmelstein, Kubovcik & Murray

[57] ABSTRACT

A pigment (or body) composed of particles having surfaces covered with a high molecular substance containing a group of the formula —COOR, where R stands for a hydrogen or metal atom, and having an acid value of at least 200 when the R in the formula stands for a hydrogen atom. It has a high power of absorbing and holding moisture. The surfaces of the pigment particles are alternatively covered with both such a high molecular substance and a substance which makes the surfaces hydrophobic. This pigment has a good affinity for oil and yet a high power of absorbing and holding moisture. A cosmetic containing any such pigment has a high moisturizing power and provides a long makeup life.

11 Claims, 1 Drawing Sheet

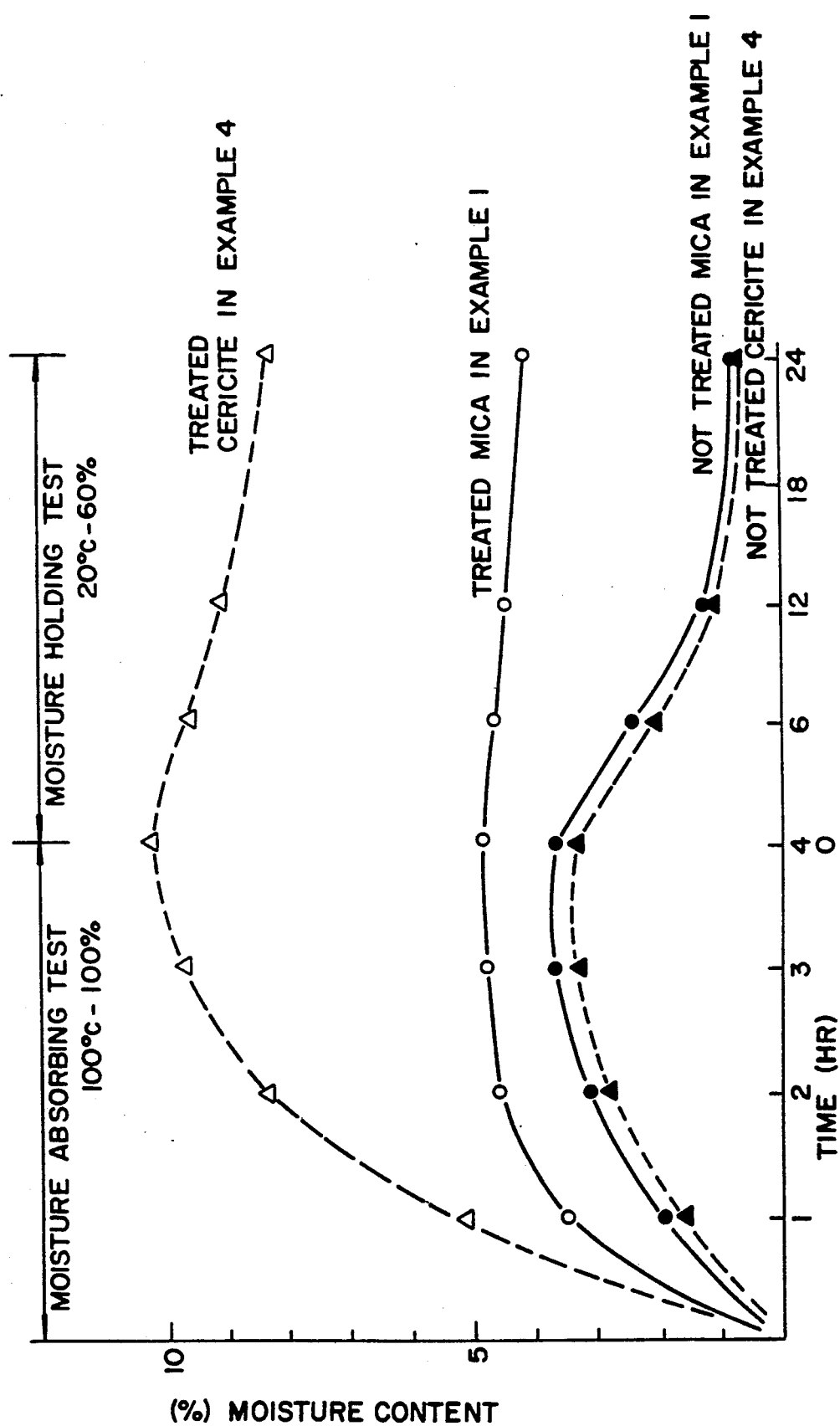

MOISTURE HOLDING PIGMENT AND A COSMETIC CONTAINING SUCH A PIGMENT

This application is a continuation of application Ser. No. 155,438 filed Feb. 12, 1988, now abandoned.

BACKGROUND OF THE INVENTION

1. Field of the Invention

This invention relates to a moisture-holding pigment and a cosmetic containing such a pigment.

2. Description of the Prior Art

There are known makeup cosmetics, such as powdery foundation, rouge and eye shadow, containing pigment or body which repels water. This property of the pigment is usually obtained by adding metal soap, or coating the surfaces of the pigment particles with silicone or metal soap. These cosmetics provide a prolonged makeup life which is not easily affected by the sweat coming out through the skin, and are also easy to mix with oil. These cosmetics have, however, the disadvantage that the skin easily loses moisture, as the pigment does not hold moisture.

Therefore, there are known makeup cosmetics containing a hydrophilic, or moisture-holding substance. The addition of such a substance, however, presents a number of problems. It lowers the affinity of a pigment for oil and causes it to change its color easily when wetted.

SUMMARY OF THE INVENTION

Under these circumstances, it is an object of this invention to provide a pigment which has an improved property of absorbing and holding moisture.

It is another object of this invention to provide a pigment which is lipophilic and yet can hold moisture.

It is still another object of this invention to provide a cosmetic having an improved property of holding moisture.

The inventors of this invention thought that it would be possible to obtain a pigment having a high power of holding moisture if the surfaces of its particles were treated with a high molecular substance having a strong power of absorbind moisture. Therefore, we have conducted an extensive series of experiments to ascertain the propriety of out concept. This invention is based on the results of these experiments.

According to a first aspect of this invention, there is provided a pigment which is composed of particles having surfaces covered with a high molecular substance containing a group of the formula —COOR, where R stands for a hydrogen or metal atom, and having an acid value of at least 200 when the R in the formula stands for a hydrogen atom. This pigment has a high power of absorbing and holding moisture.

According to a second aspect of this invention, there is provided a pigment which is composed of particles having surfaces covered with a high molecular substance as hereinabove defined, and a substance which makes those surfaces hydrophobic. This pigment is lipophilic and yet has a high power of absorbing and holding moisture.

The pigment of this invention can very advantageously be used for preparing a makeup cosmetic of the "two-way" type which is applicable to the skin by using either a wet or a dry sponge.

The cosmetic of this invention contains either of two types of pigments as hereinabove defined, and has a good property of holding moisture. In other words, it can satisfactorily moisturize the skin to which it has been applied. Moreover, it provides a makeup life which is as long as that which can be achieved by employing any known cosmetic containing a hydrophobic pigment.

Therefore, this invention is ideally applicable to makeup cosmetics, such as a powdery foundation, rouge and eye shadow. The application of the pigment according to this invention is, however, not limited to the cosmetics. It is also useful for any other field of application that calls for the maintenance of an appropriate amount of moisture.

BRIEF DESCRIPTION OF THE DRAWING

FIG. 1 is a graphical representation of the moisture absorbing and holding tests conducted in EXAMPLES 1 and 4 which will hereinafter be described.

DETAILED DESCRIPTION OF THE INVENTION

The particle surfaces of the pigment according to this invention are covered with a high molecular substance containing a group of the formula —COOR, where R stands for a hydrogen or metal atom, and having an acid value of at least 200 when it is a carboxyl group. Specific examples of the high molecular substances which can be used for the purpose of this invention include polyacrylic acid, polyglutamic acid, carboxymethyl cellulose, carboxyethyl cellulose, maleic acid-modified polyolefin, and the sodium, potassium, lithium and ammonium salts thereof. The acid value is the amount in mg of KOH which is required for neutralizing 1 g of the high molecular substance. No high molecular substance containing a carboxyl group and having an acid value which is less than 200 has a satisfactorily high power of absorbing and holding moisture. A substance having an acid value of at least 350 is particularly effective for the purpose of this invention. Polyacrylic or polyglutamic acid is, among others, preferable because of its high power of absorbing and holding moisture.

Although it is satisfactory that the surfaces of the pigment particles are merely coated with the high molecular substance, it is preferable from the standpoints of product stability, oil dispersibility, and moisture holding property that the substance in the form of a water-insoluble metal salt be adsorbed in an oriented pattern to the particle surfaces. It is desirable from the stand-point of the moisture holding property of the particles that the salt contain some free carboxyl groups instead of having metal atoms substituted for the hydrogen atoms in all of its carboxyl groups.

Referring to a method of coating the surfaces of the pigment particles with a high molecular substance containing a carboxyl group, it is dissolved in water, alcohol, a petroleum or aromatic hydrocarbon, etc., its solution and the pigment are uniformly mixed, and the pigment is dried. It is desirable to use a drying method which does not cause any substantial cohesion of the pigment particles. Therefore, it is appropriate to use, for example, a drier which employs a fluidized bed or a jet stream of air.

Referring to a method of having adsorbed to the surfaces of the pigment particles a high molecular substance containing a carboxyl group in which a metal atom is substituted for the hydrogen atom, the pigment is dispersed in water and a solution containing the high molecular substance in the amount of 1.0 to 10.0% by weight of the pigment is added to the dispersion, so that the substance is emulsified or dissolved in the water. Then, an aqueous solution of a soluble salt of Al, Mg, Ca, Zn, Zr, Ti, etc. is dropped into the emulsion or solution in an amount which is equivalent to 0.2 to 5 times as large as that of the carboxyl group. Sulfuric or hydrochloric acid can, for example, be added to neutralize a part of the sodium, potassium, lithium or ammonium salt of carboxylic acid to leave some free carboxyl groups. The high molecular substance is now insoluble in water and is completely adsorbed in an oriented pattern to the surfaces of the pigment particles. The pigment can be added directly to a liquid cosmetic, though it is usually dewatered, dried and crushed beforehand.

According to this invention, it is also possible to use in addition to any such high molecular substance a substance which makes the surfaces of the pigment particles hydrophobic, an thereby form a pigment which is lipophilic and yet can hold moisture. Specific examples of the substances which can be used for making the particle surfaces hydrophobic include silicone oil, metal soap, an acylamino acid salt, lecithin and an acylated peptide salt. It is preferable from the standpoints of easy application and a good balance of the hydrophobic and moisture holding properties to use metal soap, an acylamino acid salt, lecithin or an acylated peptide salt.

Reference is made to Japanese Laid-Open Patent Specification No. 69011/1985 for further details concerning the metal soap and a method by which it can be adsorbed to the particle surfaces, Japanese Laid-Open Patent Specification No. 72512/1983 for the acylamino acid salt, Japanese Laid-Open Patent Specification No. 184571/1985 for the lecithin, and Japanese Laid-Open Patent Specification No. 73775/1986 for the acylated peptide salt. It is possible to use one of them alone, or a mixture thereof.

The pigment particles are usually caused to adsorb the high molecular substance before the substance which make them hydrophobic, or the two substances simultaneously. If they are not applied simultaneously, the order in which they are applied should not reversed, since the substance which is used for making the particle surfaces hydrophobic prevents the high molecular substance from being uniformly applied, or fails to make the particle surfaces satisfactorily hydrophobic.

The term "pigment" as herein used covers a wide range of pigments and bodies which are used for cosmetics, or as industrial pigments. They include inorganic pigments such as titanium oxide, aluminum oxide, zinc oxide, zirconium oxide, red oxide, yellow iron oxide, black iron oxide, ultramarine blue, Prussian blue, chromium oxide and chromium hydroxide, and bodies such as talc, kaolin, muscovite, sericite, other types of mica, magnesium carbonate, calcium carbonate, aluminum silicate, magnesium silicate, calcium silicate and clays. They also include titanium mica, bismuth oxychloride, silica beads, nylon, acrylic, polyethylene or other plastic beads, tar pigments and natural pigments.

Specific examples of the soluble salts of Al, Mg, Ca, Zn, Zr, Ti, etc. which can be used for the purpose of this invention include aluminum sulfate, aluminum chloride, aluminum nitrate, potassium aluminum sulfate, magnesium chloride, magnesium sulfate, magnesium nitrate, potassium magnesium sulfate, calcium chloride, calcium nitrate, calcium acetate, zinc chloride, zinc nitrate, zinc sulfate, zinc acetate, zirconium sulfate, zirconium chloride, titanium oxysulfate and titanium tetrachloride.

The pigment or body is preferably coated with 1.0 to 10.0% by weight of the high molecular substance. If it is coated with only less than 1.0% by weight of the high molecular substance, it does not have a satisfactorily high power of holding moisture. If it is coated with over 10.0% by weight thereof, it shows an undesirable cohesion of particles.

If it is also coated with a substance which makes its particle surfaces hydrophobic, it is preferably coated with 0.5 to 5.0% by weight thereof. If it is coated with only less than 0.5% by weight thereof, it is not satisfactorily hydrophobic. If it is coated with over 5.0% by weight thereof, it shows an undesirable cohesion of particles.

The pigment which has been subjected to hydrophobic treatment has a good affinity for oil and can, therefore, be employed in a customary manufacturing process to produce a cosmetic which is smooth, makes the skin feel pleasant and yet has a high power of holding moisture.

The invention will now be described in further detail with reference to several examples thereof. These examples are, however, not intended for limiting the scope of this invention.

EXAMPLE 1

A solution was prepared by dissolving 5 g of a sodium salt of carboxymethyl cellulose (CELLOGEN 7A of Daiichi Kogyo Seiyaku K. K., Japan) in 50 g of water. The solution and 250 g of mica were mixed in a Henschel mixer. The mixture was dried and crushed in a jet-o-drier(product of Seishin Kigyo K. K., Japan) at a temperature of 80° C. and a pressure of 2 kg/cm$^2$ to yield a pigment having particle surfaces coated with the sodium salt.

Five grams of the pigment were put on an aluminum dish and the dish was placed in a steam bath having a temperature of 100° C. and a relative humidity of 100%, whereby the pigment was examined for its moisture absorbing power. The results are shown in TABLE 1 and FIG. 1. Then, it was examined for its moisture holding power in a room having a temperature of 20° C. and a relative humidity of 60%. The results are shown in TABLE 2 and FIG. 1. The results are all shown by the moisture content of the pigment in % by weight.

TABLE 1

| Moisture absorbing power (100° C.; 100% RH) | | | | |
|---|---|---|---|---|
| Hours in steam bath | 1 | 2 | 3 | 4 |
| EXAMPLE 1 | 3.5% | 4.6% | 4.8% | 4.9% |
| Mica not treated | 1.9% | 3.1% | 3.6% | 3.6% |

TABLE 2

| Moisture holding power (20° C.; 60% RH) | | | | |
|---|---|---|---|---|
| Hours in the room | 0 | 6 | 12 | 24 |
| EXAMPLE 1 | 4.9% | 4.7% | 4.5% | 4.1% |
| Mica not treated | 3.6% | 2.4% | 1.2% | 0.8% |

As is obvious from TABLES 1 and 2, the pigment embodying this invention had a higher power of absorbing and holding moisture than the mica which had not been treated.

EXAMPLE 2

An aqueous talc dispersion was prepared by dispersing 100 g of talc in one liter of water in a reactor having a stirrer. 10 g of sodium polyacrylate (ARON 20U of Toa Gosei K. K., Japan, having a solid content of 40%) were dissolved in the dispersion. Then, 22 ml of an aqueous solution containing 250 g of aluminum chloride per liter were dropped into the dispersion and it was stirred for 15 minutes. The talc was dewatered by a suction filter and dried at a temperature of 115° C. for eight hours to yield particles having surfaces to which aluminum polyacrylate had been adsorbed in an oriented pattern.

The procedure of EXAMPLE 1 was repeated for examining the moisture absorbing power of the talc in a steam bath having a temperature of 100° C. and a relative humidity of 100%. It showed an equilibrium moisture content of 9.8% six hours after it had been placed in the steam bath, when the talc which had hot been treated showed a moisture content of only 3.4%.

EXAMPLE 3

A mixed solution containing 5 g of isopropyl alcohol, 5 g of benzole and 2 g of methyl hydrogen polysiloxane (KF-99 of Shinetsu Kagaku K.K., Japan) was mixed with 100 g of the talc which had been obtained in EXAMPLE 2. The mixture was allowed to dry, whereby the solvent was removed therefrom. Then, it was heated at a temperature of 130° C. for two hours to yield a highly hydrophobic pigment.

The pigment showed a moisture content of 5.5% after six hours of exposure to a temperature of 100° C. and a relative humidity of 100%.

EXAMPLE 4

An aqueous sericite dispersion was prepared by dispersing 100 g of sericite in 500 ml of water and 3 g of sodium polyglutamate (AJICOAT spg of Ajinomoto K.K., Japan) were fully dissolved in the dispersion. Five milliliters of a 10% solution of sulfuric acid were dropped into the dispersion and 16 ml of an aqueous solution containing 200 g of zinc sulfate per liter were thereafter dropped, and the dispersion was stirred for 15 minutes.

Then, 10 g of a sodium salt of coconut oil fatty acid collagen peptide (a 30% aqueous solution of NIKKOL CCN40 of Nikko Chemical Co., Ltd., Japan) were dissolved in the dispersion, and after 10 ml of the zinc sulfate solution had been dropped again, the mixture was stirred for 15 minutes. The mixture was dewatered by a suction filter and dried at a temperature of 115° C. for eight hours to yield sericite having particle surfaces to which a partial zinc salt of polyglutamic acid and an acylated zinc salt of peptide had been adsorbed in an oriented pattern.

The sericite was hydrophobic and yet showed a high power of absorbing and holding moisture, as is obvious from FIG. 1.

EXAMPLE 5

Components 1

Sericite 50 g, talc 8 g, mica 3 g, titanium mica 3 g, titanium oxide 19 g, yellow iron oxide 3 g, red oxide 1 g, and black iron oxide 0.2 g.

They were dispersed in 500 ml of water in a reactor having a stirrer. 4.4 g of sodium polyglutamate (AJICOAT SPG of Ajinomoto K.K., Japan) and 7.3 g of a sodium salt of coconut oil fatty acid collagen peptide (a 30% aqueous solution of NIKKOL CCN-40 of Nikko Chemical Co., Ltd., Japan) were dissolved in the dispersion. Then, 30 ml of an aqueous solution containing 250 g of aluminum sulfate per liter were dropped into the solution and it was stirred for 15 minutes. The mixture was dewatered by a suction filter and dried by hot air at a temperature of 105° C. for eight hours to yield 87 g of a pigment.

Components 2

Squalane 5 g, methyl polysiloxane 3 g, isopropyl myristate 2 g, paraffin 1 g, a surface active agent 1 g, a preservative 0.2 g, and a perfume 0.5 g.

Components 1 were mixed by a Henschel mixer and the mixture was crushed by an atomizer. A hot mixture of Components 2 was placed in the crushed mixture. They were mixed by a Henschel mixer and the mixture was crushed by an atomizer. The resulting particles were put in a container and molded into a powdery foundation.

It was a powdery foundation of the two-way type having a strong power of repelling water and capable of being applied by either a dry or a wet sponge.

COMPARATIVE EXAMPLE 1

Components 1

Sericite 50 g, talc 8 g, mica 3 g, titanium mica 3 g, titanium oxide 19 g, yellow iron oxide 3 g, red oxide 1 g, and black iron oxide 0.2 g.

They were carefully mixed. The mixture was added to a solution which had been obtained by dissolving 1.75 g of methyl hydrogen polysiloxane in 15 g of benzene. They were mixed by a domestic mixer for five minutes. The mixture was allowed to dry at an ordinary room temperature, whereby benzene was completely removed therefrom. Then, it was fired at a temperature of 120° C. for three hours.

Components 2

Squalane 5 g, methyl polysiloxane 3 g, isopropyl myristate 2 g, paraffin 1 g, surface active agent 1 g, preservative 0.2 g, and perfume 0.5 g.

Components 1 were mixed by a Henschel mixer and the mixture was crushed by an atomizer. A hot mixture of Components 2 was placed in the crushed mixture. They were mixed by a Henschel mixer and the mixture was crushed by an atomizer. The resulting particles were put in a container and molded into a powdery foundation.

It was a powdery foundation of the two-way type having a strong power of repelling water and capable of being applied by either a dry or a wet sponge.

It was compared in certain properties with the foundation of EXAMPLE 5. The results are shown in TABLE 3.

TABLE 3

|  | EXAMPLE 5 | COMPARATIVE EXAMPLE 1 |
|---|---|---|
| Adhesion | ⊚ | Δ |
| Extensibility | ○ | ⊚ |
| Moisture holding power (Moisturizing effect) | ⊚ | Δ |

⊚ : Very good
○: Good
Δ: Poor

What is claimed is:
1. Pigment particles wherein the surfaces of the particles are covered with a water-insoluble, water-absorbent polymeric substance containing a group of the formula —COOR, wherein R is a metal atom selected from the group consisting of aluminum, magnesium, calcium, zinc, zirconium and titanium, the amount of said polymeric substance being from 1.0 to 10.0% by weight of said particles, wherein said surfaces are additionally covered with a substance which renders said surfaces hydrophobic.

2. Pigment particles as in claim 1, wherein said polymeric substance is adsorbed in an oriented pattern to said surfaces.

3. Pigment particles as in claim 1, wherein said polymeric substance containing a group —COOR is selected from the group consisting of polyacrylic acid, polyglutamic acid, and sodium, potassium, lithium and ammonium salts thereof.

4. Pigment particles as in claim 1, wherein said substance which renders said surfaces hydrophobic is a metal salt of an acid.

5. Pigment particles as in claim 4, wherein both the water-insoluble, water-absorbent polymeric substance and the substance which renders said surfaces hydrophobic are adsorbed in an oriented pattern to said surfaces.

6. Pigment particles as in claim 1, wherein said polymeric substance containing a group —COOR, is selected from the group consisting of polyacrylic acid, polyglutamic acid, carboxymethylcellulose, carboxyethylcellulose, maleic acid-modified polyolefins, and sodium, potassium, lithium and ammonium salts therof.

7. Pigment particles as in claim 1, wherein said polymeric substance containing a group —COOR, is selected from the group consisting of polyacrylic acid, polyglutamic acid, and sodium, potassium, lithium and ammonium salts thereof.

8. Pigment particles as in claim 1, wherein said substance which makes said surfaces hydrophobic is selected from the group consisting of metal soap, an acylamino acid salt, and an acylated peptide salt.

9. A cosmetic containing pigment particles wherein the surfaces of the particles are covered with a water-insoluble, water-absorbent polymeric substance containing a group of the formula —COOR, wherein R is a metal atom selected from the group consisting of aluminum, magnesium, calcium, zinc, zirconium and titanium, the amount of said polymeric substance being from 1.0 to 10.0% by weight of said particles, wherein said surfaces are additionally covered with a substance which renders said surfaces hydrophobic.

10. A cosmetic as in claim 9, wherein said polymeric substance containing a group —COOR, is selected from the group consisting of polyacrylic acid, polyglutamic acid, and sodium, potassium, lithium and ammonium salts thereof.

11. A cosmetic as in claim 9, wherein said polymeric substance containing a group —COOR, is selected from the group consisting of polyacrylic acid, polyglutamic acid, carboxymethylcellulose, carboxyethylcellulose, maleic acid-modified polyolefins, and sodium, potassium, lithium and ammonium salts thereof.

* * * * *